(12) United States Patent
Leung et al.

(10) Patent No.: US 10,513,725 B2
(45) Date of Patent: Dec. 24, 2019

(54) PUBLIC PERSONALIZED MOBILE HEALTH SENSING SYSTEM, METHOD AND DEVICE

(71) Applicant: eNano Health Limited, Hong Kong (HK)

(72) Inventors: Patrick Shau-park Leung, Arcadia, CA (US); Chi Tao Leung, Arcadia, CA (US)

( * ) Notice: Subject to any disclaimer, the term of this patent is extended or adjusted under 35 U.S.C. 154(b) by 0 days.

(21) Appl. No.: 15/469,138

(22) Filed: Mar. 24, 2017

(65) Prior Publication Data

US 2017/0247743 A1 Aug. 31, 2017

Related U.S. Application Data

(63) Continuation-in-part of application No. 15/056,163, filed on Feb. 29, 2016.

(51) Int. Cl.
| | | |
|---|---|---|
| *C12Q 1/26* | (2006.01) | |
| *A61B 10/00* | (2006.01) | |
| *C12Q 1/28* | (2006.01) | |
| *C12Q 1/54* | (2006.01) | |

(52) U.S. Cl.
CPC ............ *C12Q 1/26* (2013.01); *A61B 10/0051* (2013.01); *C12Q 1/28* (2013.01); *C12Q 1/54* (2013.01)

(58) Field of Classification Search
CPC .......... C12Q 1/26; C12Q 1/28; A61B 10/0051
See application file for complete search history.

(56) References Cited

U.S. PATENT DOCUMENTS

| | | | | |
|---|---|---|---|---|
| 5,714,341 A | * | 2/1998 | Thieme | G01N 33/558 422/417 |
| 2013/0273528 A1 | * | 10/2013 | Ehrenkranz | G01N 33/54366 435/6.1 |
| 2014/0235963 A1 | * | 8/2014 | Edwards | A61B 5/0022 600/301 |
| 2014/0296089 A1 | * | 10/2014 | Holmes | G01N 35/026 506/9 |
| 2015/0359458 A1 | * | 12/2015 | Erickson | G01N 33/52 455/557 |

OTHER PUBLICATIONS

University of Cambridge. "Pocket diagnosis: App turns any smartphone into a portable medical diagnostic device." ScienceDaily. ScienceDaily, Mar. 19, 2014. ww.sciencedaily.com/releases/2014/03/140319103612.htm (Year: 2014).*

* cited by examiner

*Primary Examiner* — Dennis White
(74) *Attorney, Agent, or Firm* — Bioinnovation Legal PLLC; James Christopher Schroeder

(57) ABSTRACT

The claimed invention relates to an enhanced mobile health detection and monitoring system utilizing non-invasive saliva screening of real-time health metrics coupled with remote deep analysis of body characteristics. Health information is derived from a combination of local chemical markers which are optically collected, locally reported and broadcast over a 'cloud based' internet data distribution system. The disclosed system, method and related device derives personal health and wellness information by combining saliva with disposable wellness indicators which are subsequently analyzed for pharmaceutical indicators as well as DNA, RNA and protein biomarkers to provide comprehensive wellness information.

3 Claims, 3 Drawing Sheets

101   103            105  107  109

PUBLIC PERSONALIZED MOBILE HEALTH SENSING SYSTEM, METHOD AND DEVICE

TECHNICAL FIELD

The claimed invention relates to acquisition, interpretation and reporting of health and wellness data. Particular embodiments of the claimed invention include saliva based wellness information collected from disposable end-user administered sample devices which are subsequently analyzed for pharmaceutical and biological markers.

BACKGROUND ART

While a number of end-user systems and devices exist to provide health and wellness information such as glucose levels, body invasive techniques including finger prick blood collection are still required. As a result, large population subsets are unwilling or unable to perform regular sample collection required to provide useful real-time health and wellness data.

At the opposite end of the wellness data spectrum, despite the rapid advancement of analytical chemistry techniques and genetic sequencing technologies the end-user has been largely left behind and is not provided with meaningful wellness data based upon their own body analysis.

SUMMARY OF INVENTION

Technical Problem

Current sources of wellness data including glucose level sensing are invasive and painful to collect resulting in lower adoption rates and reduced patient engagement. Detailed health and wellness biomarkers and chemical analysis have cost and complexity constraints and are generally limited to highly specialized health industry service professionals. From a data analytics and wellness information communication perspective, real-time wellness data is often not linked to high level biomarker screening and not communicated to an end-user in a meaningful way to enable lifestyle changes enhancing wellness.

Solution to Problem

The presently claimed invention leverages mobile computing platforms in both localized and cloud computing embodiments together with acquisition and reporting of high value health and wellness data obtained through non-invasive means. Non-invasive saliva sample collection provides 'on the spot' health metrics with increased quality control measures and enhanced by subsequent sample analysis. Personal wellness information is interpreted and communicated through cloud computing means so that the end-user can implement meaningful lifestyle change for improved health and wellness.

Advantageous Effects of Invention

End-user health information such as glucose levels are gateway opportunities to engage the user to broaden infrequent 'snapshot' health metrics into a more informative and deeper understanding of body wellness. The claimed invention is an 'additive' wellness system with synergistic effects from components. The end-user captured glucose levels are interpreted by 'smartphone' devices enabling deeper reporting and analytics. The subsequent analysis of the disposable glucose sensing devices provide deep wellness screening ability by sensing pharmaceutical and carrier detection as well as the rapidly expanding knowledge derived from DNA, RNA and protein fragments present in saliva bodily fluids. The end user's initial engagement of 'how much sugar can I eat' is rapidly expanded to 'did I forget to take my pills today' enhanced by robust biomarker details.

Embodiments of the claimed invention include social media components for reporting of health updates and alerts to loved ones and trusted health care providers. Elderly patients at risks from high and low glucose sensitivity can update not only their own wellness information but include family members able to intervene and provide wellness support and critical lifestyle management opportunities.

BRIEF DESCRIPTION OF DRAWINGS

The accompanying drawings are included to better illustrate exemplary embodiments of the claimed invention.

DESCRIPTION OF EMBODIMENTS

Examples

P4 Medicine is Predictive, Preventive, Personalized and Participatory. Its two major objectives are to quantify wellness and demystify disease. In the illustrative examples contained herein, the aims of P4 Medicine are achieved by combining end-user analysis of current health metrics together with follow-on lab analytics of the same saliva sample. Color changes are measured by smartphone to report glucose levels to the end-user for personalized and participatory wellness monitoring. The same test strip subsequently analyzed using standard analytical equipment, however, provides the opportunity for predictive and preventative health screening based upon detection of pharmaceuticals and their carriers as well as DNA, RNA and protein indicators of body health as well as the presence or absence of harmful bacteria, viruses and other disease carriers.

Example 1

Figure 1:
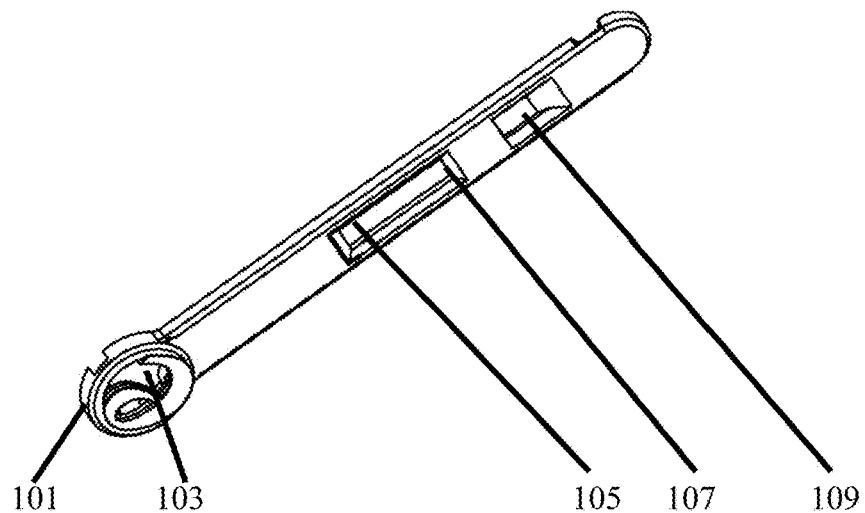
FIG. 1 shows an illustrative embodiment of a health sample collection device with sample collection housing and one or more chemical sensors and positive sample reporting means.

In a first illustrative embodiment of the claimed invention, a user seeking to monitor wellness information and measure glucose levels obtains a saliva sample using a device as illustrated in FIG. 1. The saliva collection device contains diagnostic reagents for both qualitative and quantitative analysis of salivary glucose. The presence of glucose in salivary induces a color change, from colorless to red, in a test strip. pH dye is used to detect the pH of the saliva. Color changes depending on the pH of the saliva and glucose changes from white to pink.

The detection of salivary glucose is based on a coupling reaction between glucose oxidase and peroxidase. Glucose oxidase oxidizes the salivary glucose into gluconolactone and hydrogen peroxide ($H2O2$). In the presence of peroxidase, 10-acetyl-3,7-dihydroxyphenoxazine reacts with H2O2 in a 1:1 stoichiometry in order to produce a white to pink color. In a preferred embodiment, the chemical sensor is a compound having the following structural formula:

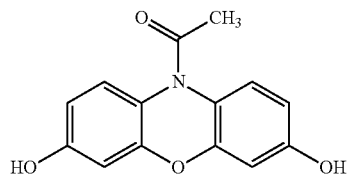 [SMILES: CC(=O)N1c2ccc(O)cc2Oc2cc(O)ccc21]

Upon exposure to the chemical sensor in the disposable substrate and sample collection housing, visual readings are taken by a smartphone device and used to determine corresponding health and wellness information and report the salivary glucose levels back to the user. The association between the saliva sample and smartphone occurs by way of a machine readable bar code upon the FIG. 1 device or device packaging, however, alternate sample linking means may be used such as RFID, Bluetooth and Near Field Communications. In the illustrative embodiment the glucose levels are reported by cellphone color strip analysis as 'high/low/normal' or a numerical reading as desired.

Example 2

In a further illustrative embodiment, the claimed system and related method gains expanded functionality when the system user returns the FIG. 1 device for further analysis. Unlike invasive blood samples which are perishable and degrade quickly over time, saliva samples are stable at room temperature and offer an extended view into the wellness and health of the user. After a user mails the device to a central analytical center, further analysis of the user's saliva sample takes place.

Using standard laboratory equipment such as liquid chromatography/mass spectrometry (LC/MS), the user's saliva sample can be screened for the presence of particular pharmaceutical products, metabolic byproducts as well as pharmaceutical carriers. In addition, by utilizing standard gene sequencing equipment screening for DNA and RNA segments, particular genetic markers for bacterial and viral pathogens are undertaken along with tissue and organ specific disease markers based upon short reads of DNA and RNA and quantitatively analyzed.

While the first illustrative embodiment is capable of operating as a stand-alone health and wellness system and method, the second illustrative embodiment incorporates cloud computing to further analyze and report the user's health and wellness screening particulars to the user's smartphone device. In the second illustrative example, when a user subsequently checks salivary glucose levels the wellness report may be augmented by health screening information derived from LC/MS analysis of the disposable salivary sample as well as genetic sequencing information. An illustrative example of a cloud computing enabled wellness report informs the user as follows: "Your salivary glucose level as of (time & date) is 'high'. Based upon the wellness screening of your previous five samples, it appears that you may not have taken your (brand name product) pharmaceutical regularly as prescribed. In addition, based upon your micro-RNA levels corresponding to liver health, you may wish to restrict your alcohol intake at this time." As a direct and intended consequence of the second illustrative embodiment, the user may select to receive 'natural language' wellness screening information in addition to or exclusion of the underlying numerical data from which the wellness readings are derived.

In a third illustrative embodiment of the claimed invention, wellness screening information may be reported in a one to many configuration by utilizing direct communication or social media channels. The health and wellness information may be reported as a 'health alert' to a dedicated medical care provider as well as an update to family members. In the third illustrative example, a dedicated health caretaker is alerted to the fact that the person in their care does not appear to be taking their prescribed medication on a regular basis, or in the alternate the care professional can be informed as to the excessive amount of pharmaceutical or carrier present in regularly analyzed saliva samples indicating an excessive administration of therapeutic agent.

In the following description, numerous specific details are set forth in order to provide a thorough understanding of the present embodiments. It will be apparent, however, to one having ordinary skill in the art that the specific detail need not be employed to practice the present embodiments. In other instances, well-known materials or methods have not been described in detail in order to avoid obscuring the present embodiments.

Reference throughout this specification to "one embodiment", "an embodiment", "one example" or "an example" means that a particular feature, structure or characteristic described in connection with the embodiment or example is included in at least one embodiment of the present embodiments. Thus, appearances of the phrases "in one embodiment", "in an embodiment", "one example" or "an example" in various places throughout this specification are not necessarily all referring to the same embodiment or example. Furthermore, the particular features, structures or characteristics may be combined in any suitable combinations and/or sub-combinations in one or more embodiments or examples. In addition, it is appreciated that the figures provided herewith are for explanation purposes to persons ordinarily skilled in the art and that the drawings are not necessarily drawn to scale.

Embodiments in accordance with the present embodiments may be implemented as an apparatus, method, or computer program product. Accordingly, the present embodiments may take the form of an entirely hardware embodiment, an entirely software embodiment (including firmware, resident software, micro-code, etc.), or an embodiment combining software and hardware aspects that may all generally be referred to herein as a "module" or "system." Furthermore, the present embodiments may take the form of a computer program product embodied in any tangible medium of expression having computer-usable program code embodied in the medium.

Any combination of one or more computer-usable or computer-readable media may be utilized. For example, a computer-readable medium may include one or more of a portable computer diskette, a hard disk, a random access memory (RAM) device, a read-only memory (ROM) device, an erasable programmable read-only memory (EPROM or Flash memory) device, a portable compact disc read-only memory (CDROM), an optical storage device, and a magnetic storage device. Computer program code for carrying out operations of the present embodiments may be written in any combination of one or more programming languages.

Embodiments may also be implemented in cloud computing environments. In this description and the following claims, "cloud computing" may be defined as a model for enabling ubiquitous, convenient, on-demand network access to a shared pool of configurable computing resources (e.g., networks, servers, storage, applications, and services) that can be rapidly provisioned via virtualization and released with minimal management effort or service provider interaction, and then scaled accordingly. A cloud model can be composed of various characteristics (e.g., on-demand self-service, broad network access, resource pooling, rapid elasticity, measured service, etc.), service models (e.g., Software as a Service ("SaaS"), Platform as a Service ("PaaS"), Infrastructure as a Service ("IaaS"), and deployment models (e.g., private cloud, community cloud, public cloud, hybrid cloud, etc.).

The flowchart and block diagrams in the flow diagrams illustrate the architecture, functionality, and operation of possible implementations of systems, methods, and computer program products according to various embodiments of the present embodiments. In this regard, each block in the flowchart or block diagrams may represent a module, segment, or portion of code, which comprises one or more executable instructions for implementing the specified logical function(s). It will also be noted that each block of the block diagrams and/or flowchart illustrations, and combinations of blocks in the block diagrams and/or flowchart illustrations, may be implemented by special purpose hardware-based systems that perform the specified functions or acts, or combinations of special purpose hardware and computer instructions. These computer program instructions may also be stored in a computer-readable medium that can direct a computer or other programmable data processing apparatus to function in a particular manner, such that the instructions stored in the computer-readable medium produce an article of manufacture including instruction means which implement the function/act specified in the flowchart and/or block diagram block or blocks.

As used herein, the terms "comprises," "comprising," "includes," "including," "has," "having," or any other variation thereof, are intended to cover a non-exclusive inclusion. For example, a process, article, or apparatus that comprises a list of elements is not necessarily limited to only those elements but may include other elements not expressly listed or inherent to such process, article, or apparatus.

Additionally, any examples or illustrations given herein are not to be regarded in any way as restrictions on, limits to, or express definitions of any term or terms with which they are utilized. Instead, these examples or illustrations are to be regarded as being described with respect to one particular embodiment and as being illustrative only. Those of ordinary skill in the art will appreciate that any term or terms with which these examples or illustrations are utilized will encompass other embodiments which may or may not be given therewith or elsewhere in the specification and all such embodiments are intended to be included within the scope of that term or terms. Language designating such nonlimiting examples and illustrations includes, but is not limited to: "for example," "for instance," "e.g.," and "in one embodiment."

INDUSTRIAL APPLICABILITY

The claimed invention has industrial applicability in the healthcare industry. With greater particularity, embodiments of the claimed invention have applicability to consumer health and wellness screening for glucose levels and related pharmaceutical monitoring and administration.

CITATION LIST

Patent Literature

This patent application is a continuation-in-part and claims priority to U.S. patent application Ser. No. 15/056,163 filed Feb. 29, 2016 to Patrick Shau-park Leung entitled "Mobile automated health sensing system, method and device."

DRAWINGS

FIG. 1 shows health sample collection device (101) with sample collection area (103) which collects and channels the user's saliva (not shown) to one or more chemical sensors (not shown). In the improved illustrative example, high saliva sample sufficiency is obtained when adequate saliva in sample channel reaches color bar (107) undergoing a color change to indicate adequate sample collection. After saliva sample (not shown) hybridizes with chemical sensors (not shown) results are reported in results window (105) for capture, analytics and reporting via smartphone (not shown). In an illustrative example, smartphone enabled wellness information capture is aided by unique sample collection device identifier (not shown) bar code. In an alternate illustrative example, additional results of alternate health measurements and/or parallel results may be optionally reported in optional results window (109).

Figure 2:
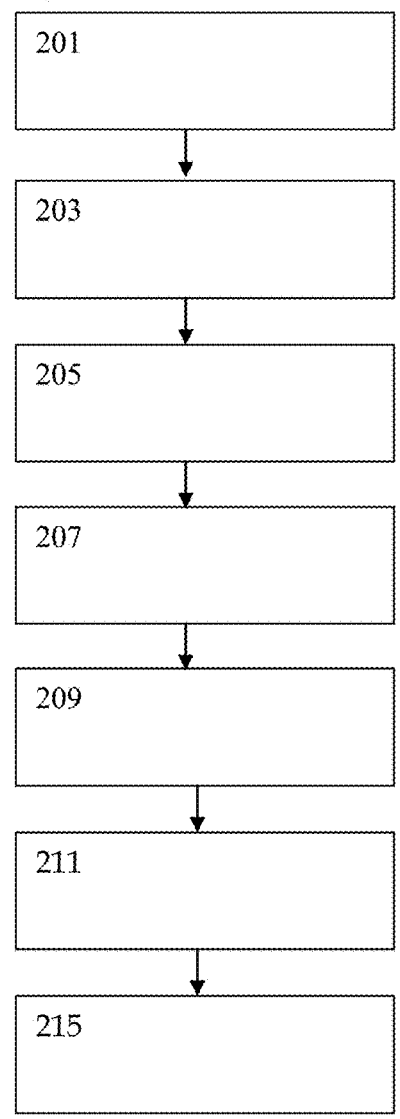
FIG. 2 is a flow diagram of illustrative health information data capture method according to the claimed invention.

FIG. 2 is a flow diagram of illustrative health information data capture method according to the claimed invention. Sample capture step (201) exposes sample (not shown) to health sample collection device (not shown) and begins exposure time calculation on smartphone (not shown). Depending upon the particular health sample under analysis, exposure time may be a critical step in determining accurate health measurements.

After sample capture step (201) results in the appropriate exposure time as determined by the smartphone (not shown), results photo capture step (203) takes place with one or more photos taken of the health sample collection device (not shown) incorporating the chemical based sensors with reporting indicators (not shown).

Color determination step (205) normalizes sample results (not shown) against optical data standardization bar (not shown) on the health sample collection device (not shown). During color determination step (205) color based results are normalized to yield standardized results regardless of mobile device camera or brand utilized. Results may be further optimized through background removal step (207) where background noise is removed.

Results association step (209) reads the QR code (not shown) on health sample collection device (not shown) or device packaging (not shown) and links data from sample capture to an individual health and wellness profile. User privacy is maintained as a direct and intended consequence of the illustrative example. Should a health sample collection device be misplaced or stolen, user identity cannot be determined solely by physical examination of a particular device.

Results interpretation step (211) matches chemical sensor display data (not shown) with a corresponding user and reports the results back on the smartphone device. Results interpretation may be derived from cloud based computing (not shown) or in the alternate on a particular smartphone device. In Remote analysis step (215) saliva sample interpretation is extended by the return or forwarding of the saliva sample to undergo further analytical processing via equipment such as LC/MS and genetic sequencing. As a result of the disclosed system and method, a novel and robust platform for personal health determination maintains privacy while allowing for specific results data sharing locally and over cloud based computing and telephony networks as desired.

Figure 3:
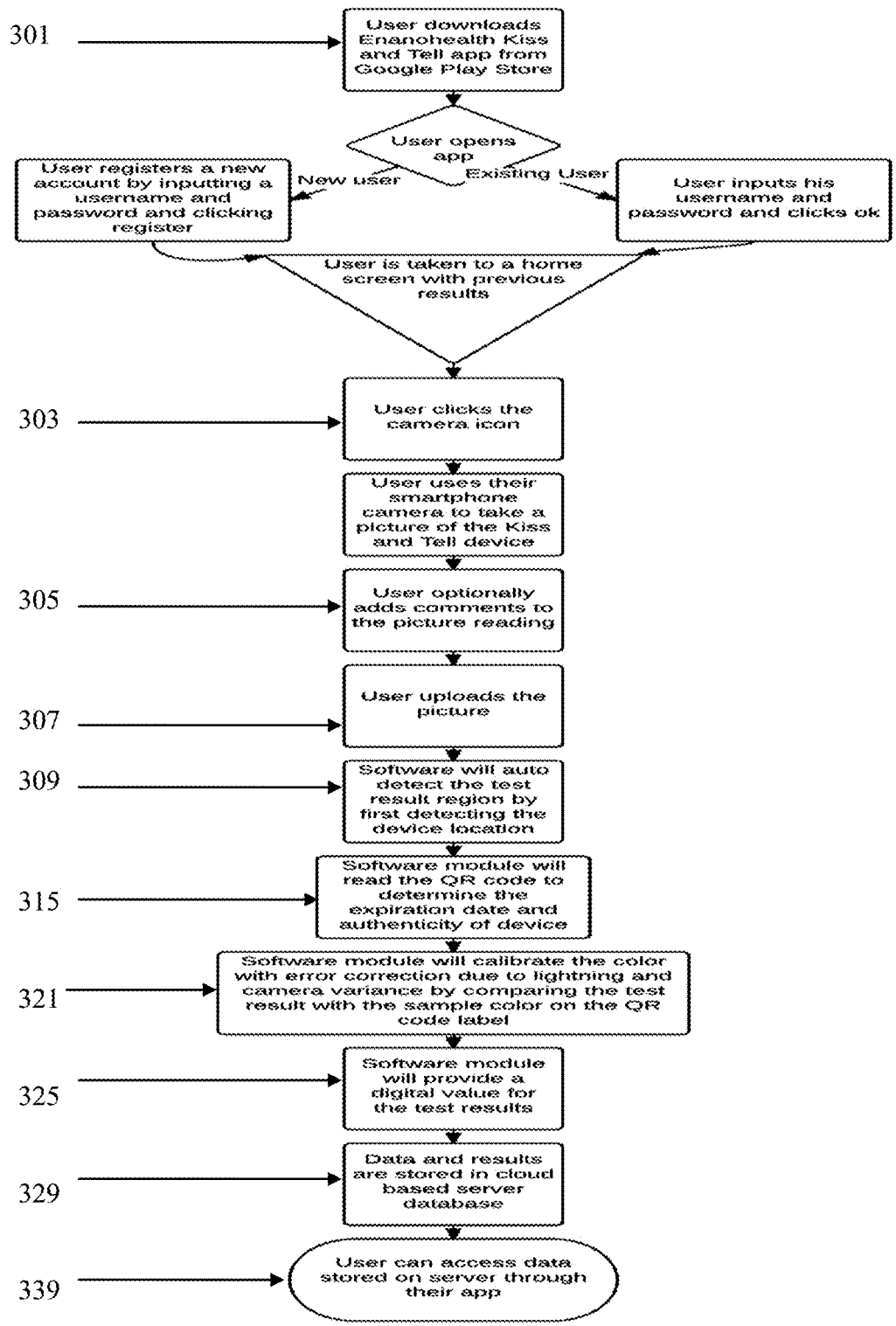
FIG. 3 is a flow diagram further illustrating health information data capture method according to the claimed invention.

FIG. 3 is an enhanced flow diagram of illustrative health information data capture method according to the claimed invention expanded to include device registration and data reporting feature sets. Device configuration step (301) downloads software to user smartphone (not shown) and if needed assigns user with a unique user id and password. Once logged in the user may be presented with previous results, comments and interpretation. Data capture step (303) begins with the user manually selecting the camera icon (not shown) within the application. Optional comment step (305) incorporates user comments into the specific data set getting captured.

Uploading step (307) uploads the captured picture (not shown) to the user smartphone (not shown) for results interpretation. Location identification step (309) takes place with smartphone software auto-detection of test result region through device location determination.

Authentication step (315) optically reads device QR code (not shown) using a software module to determine the expiration data and authenticity of device.

Optional error correction step (321) calibrates photo color with error correction to correct for lighting and camera variances by comparing the test result with the sample color bar on the QR code label.

Results reporting step (325) provides a digital value for the test results which may be graphically depicted on the user smartphone (not shown).

Results uploading step (329) transmits data, results and any optional comments to a cloud based server database (not shown).

User data access step (339) may take place on smartphone (not shown) to display data via the user application (not shown) taken from either cloud based or locally stored results.

Figure 4:
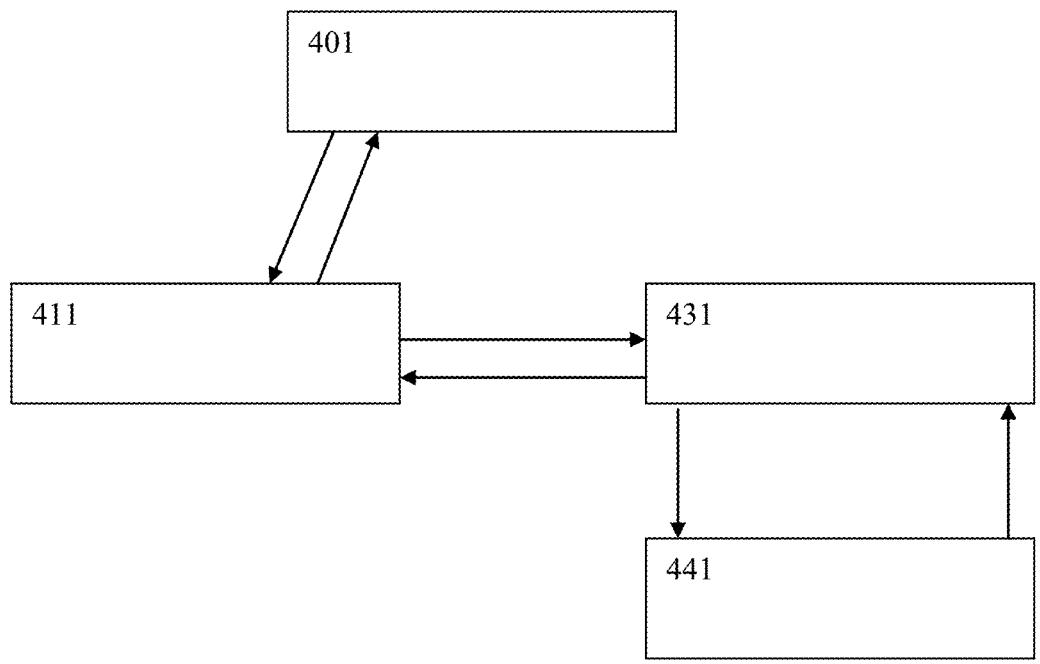
FIG. 4 is a schematic representation of the wellness system component elements.

FIG. 4 is a schematic representation of an illustrative example of the wellness system component elements. Health sample collection device (401) captures user samples (not shown) and chemical based sensors which are hybridized together.

In the presence of a positive sample, results are measurable by a computing device such as a smartphone (411). Results data capture may take place by optical measurement of smartphone (411) and in alternate foreseeable variants may also take place through near field communication wireless transmission. Smartphone (411) not only captures and transmits results but also displays results as well. While results may be locally interpreted, it is a direct and intended consequence of the illustrative example that results are uploaded to one or more cloud computing elements (431) for data interpretation and sharing.

Results provided by smartphone (411) may include specific wellness data such as glucose levels but also may include data history as well as correlation between data results and pharmaceutical requirements of the user. Alerts based upon missed pharmaceutical dosing may be alerted to the user by utilization of timing functions. Present and future dosing optimization may be provided based upon results interpretation. Near field communication readings may alert the user to the presence or absence of sufficient pharmaceutical dosing by reading RFID labels or tags (not shown) corresponding to proscribed pharmaceuticals in the immediate presence of the user.

Communications in the illustrative system may take place by each element including cloud (431) based, smartphone (411) based and health sample collection device (401) based. Cloud (431) based embodiments may not only send health results to smartphone (411) but also to health care medical providers (not shown) and friends and family (not shown). Smartphone (411) reporting may alert not only the user (not shown) but also provide automated audible and visual alerts in the case of an incapacitated user. In another alternate and foreseeable variant, health sample collection device (401) may provide immediate results feedback to the user (not shown) by way of physical means such as haptic feedback.

Additional analysis in the illustrative system may take place through the additional analysis center (441) interpretation of the saliva sample form collection device (401) which is then linked via cloud computing (431) to smartphone (411). Additional analysis can be performed using standard laboratory equipment upon a saliva sample which has been returned by the user. Liquid Chromatography/Mass Spectroscopy (LC/MS) screening for pharmaceutical compounds (both legal and illicit) as well as pharmaceutical carriers can be undertaken to determine pharmaceutical product administration as well as misadministration. Subsequent genetic sequence analysis of the saliva for DNA and RNA markers for disease and wellness levels of body health and pathogen presence or absence in the saliva sample can also be undertaken. Analytical results can be shared directly with smartphone (411) as well as to authenticated and trusted third party individuals such as dedicated medical health care providers and family members via phone alert, email and social media.

We claim:

1. A personal health monitoring system consisting of:
   A saliva sample collection device with one or more glucose in saliva health sample detection chemicals which in the presence of peroxidase, 10-acetyl-3,7-dihydroxyphenoxazine reacts with $H_2O_2$ in a 1:1 stoichiometry to produce a red color change in the presence of glucose in a saliva sample, a personal communication smartphone device incorporating one or more central processing units configured to interpret glucose in saliva, one or more cameras, internet connection means and near field wireless communication means, health sample interpretation software programmed to detect color change of glucose in saliva detection chemicals, and a cloud computing element for interpretation and communication of glucose in saliva sample health care results and additional analytical liquid chromatography and mass spectrometry means for further health and wellness analysis of saliva sample collection device.

2. A personal health monitoring system consisting of:
   A saliva sample collection device with one or more glucose in saliva health sample detection chemicals with a compound having the following structural formula:

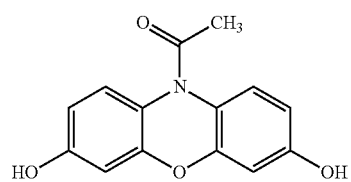 [SMILES: CC(=O)N1c2ccc(O)cc2Oc2cc(O)ccc21]

which in the presence of peroxidase, 10-acetyl-3,7-dihydroxyphenoxazine reacts with $H_2O_2$ in a 1:1 stoichiometry to produce a red color change in the presence of glucose in a saliva sample, a personal communication smartphone device incorporating one or more central processing units configured to interpret glucose in saliva, one or more cameras, internet connection means and near field wireless communication means, health sample interpretation software programmed to detect color change of glucose in saliva detection chemicals, and a cloud computing element for interpretation and communication of glucose in saliva sample health care results and additional analytical liquid chromatography and mass spectrometry means for further health and wellness analysis of saliva sample collection device.

3. A method for personal health data collection consisting of the steps of: Exposing a saliva sample by an end user to one or more salivary glucose biosensors which in the presence of peroxidase, 10-acetyl-3,7-dihydroxyphenoxazine reacts with $H_2O_2$ in a 1:1 stoichiometry to produce a red color change in the presence of glucose in the saliva sample, Smartphone capturing data derived from glucose in saliva biosensor reporting by an end user, Interpreting data captured from glucose in saliva biosensors, and Uploading data to cloud based data interpretation, storage and reporting resources after said smartphone capturing data derived from glucose in saliva step, Reporting health and wellness information derived from data from glucose in saliva biosensors to an end user subject in need thereof, and Further analyzing said saliva sample for pharmaceutical, pharmaceutical carrier and biological wellness indicators utilizing liquid chromatography, mass spectroscopy and genetic sequencing.

* * * * *